Jan. 1, 1957 F. W. ANDERSON Plant Pat. 1,544

NECTARINE TREE

Filed Feb. 20, 1956

WITNESS

Addison E. Avery

INVENTOR

Frederic W. Anderson

Webster & Webster

ATTYS.

United States Patent Office

Plant Pat. 1,544
Patented Jan. 1, 1957

1,544

NECTARINE TREE

Frederic W. Anderson, Merced, Calif.

Application February 20, 1956, Serial No. 566,744

1 Claim. (Cl. 47—62)

This invention relates to a new and distinct variety of nectarine tree which bears large, red, clingstone fruit; the primary characteristic of the variety being that its fruit—which generally resembles the Red Grand nectarine (United States Plant Patent No. 1,060)—comes into harvest approximately two weeks later.

The Red Grand nectarine has enjoyed very substantial commercial success, and the present variety provides a fruit of comparable quality on the market closely following such Red Grand nectarine.

The present variety of nectarine tree is further characterized by a ripening period which is approximately one week later than the Le Grand nectarine (United States Plant Patent No. 549), but here the fruit has a more attractive red exterior color.

The instant variety of nectarine tree was originated by me in my experimental orchard near Le Grand, Merced County, California, in the following manner:

A large number of open-pollinated seedlings of the Red Grand nectarine were grown, and upon careful inspection and observation it was ascertained that one of such seedlings had especial possibilities as a commercial variety; this particularly by reason of its ripening period.

I therefore selected such one seedling, which is the present variety, for asexual reproduction, which was accomplished—in my experimental orchard, located as aforesaid—by top-working by budding on mature orchard trees. Such asexual reproductions—when they came into bearing—were found to carry forward each and every characteristic of the parent seedling.

Figure 1:
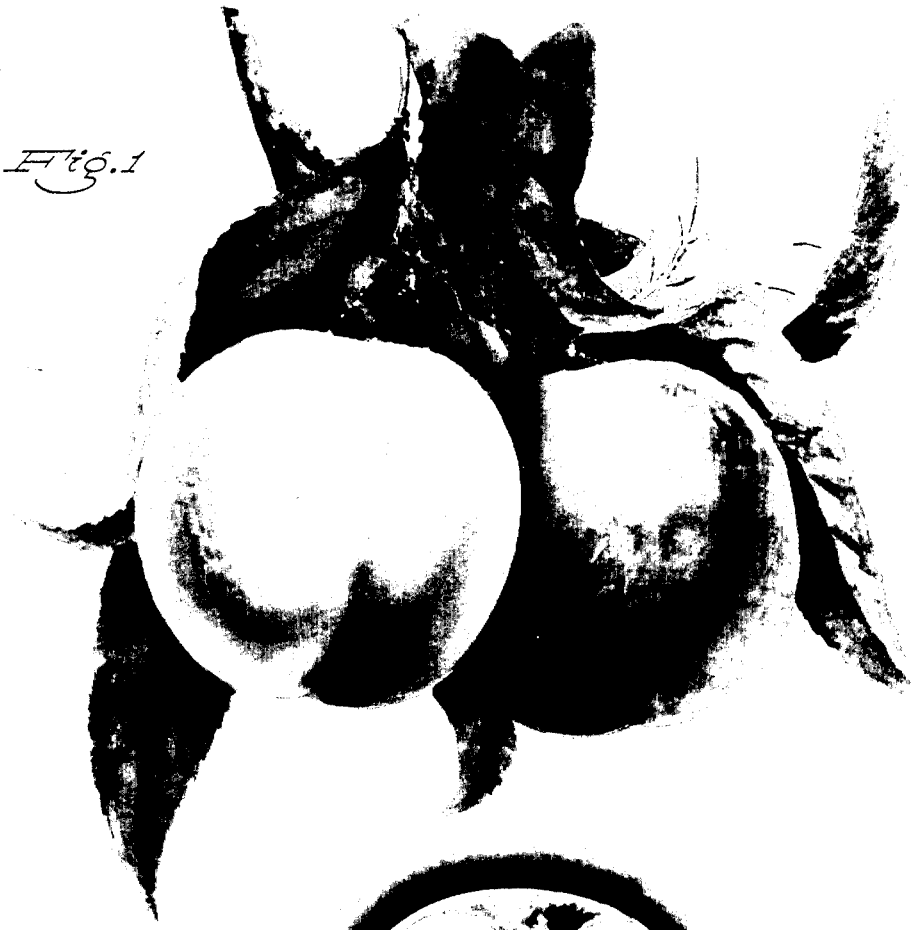
Fig. 1 is an elevation showing two of the fruit, together with twigs and leaves.
Figure 2:
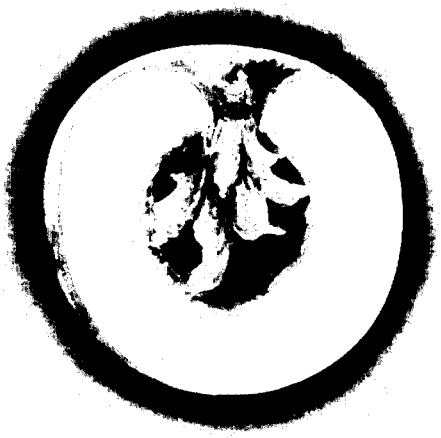
Fig. 2 is a sectional elevation of one of the fruit with the stone exposed.

Referring now more specifically to the pomological details of this new and distinct variety of nectarine tree, the following is an outline description thereof; all major color plate identifications being by reference to Maerz and Paul Dictionary of Color:

Tree:
- *Size.*—Medium.
- *Vigor.*—Medium.
- *Growth.*—Spreading.
- *Production.*—Very productive.

Trunk:
- *Size.*—Medium.
- *Texture.*—Medium.

Branches:
- *Size.*—Medium.
- *Texture.*—Medium.
- *Lenticels.*—Medium number.

Leaves:
- *Size.*—Large. Average length—6 to 6¾"; average width 1⅝" to 1 13/16".
- *Thickness.*—Medium.
- *Margin.*—Crenate.

- *Petiole.*—Medium length.
- *Glands.*—Average number—four. Alternate; reniform. Position—usually two on petiole and several on blade.
- *Stipules.*—Lacking.
- *Color.*—Top side—medium green (22–L–6); under side—lighter green (21–J–6).

Flower buds:
- *Size.*—Medium.
- *Length.*—Medium.
- *Form.*—Plump.

Flowers:
- *First and full bloom.*—Approximately with the Elberta peach (unpatented). Medium blooming period as compared with other varieties.
- *Size.*—Large.

Fruit:
- *Maturity when described.*—Eating ripe.
- *Date of first picking.*—August 8, 1955.
- *Date of last picking.*—August 18, 1955.
- *Size.*—Uniform; large. Average diameter axially—3¼". Average transversely in suture plane—3¼".
- *Form.*—Uniform; globose.
- *Suture.*—Shallow, with slight depression beyond pistil point.
- *Ventral surface.*—Rounded.
- *Cavity.*—Rounded. Average depth—⅜", average breadth—¾". Markings—red.
- *Base.*—Flat.
- *Apex.*—Short; depressed.
- *Pistil point.*—Lacking.

Skin:
- *Thickness.*—Thick.
- *Texture.*—Tough.
- *Tenacity.*—Tenacious to flesh.
- *Tendency to crack.*—None.
- *Down.*—Wanting.
- *Color.*—Yellow (11–H–7), almost completely overspread with red (1–K–11, shading to 5–L–12), with some motting, sometimes tending to shade to a deep red (56–L–12).

Flesh:
- *Texture.*—Firm; fine; meaty.
- *Fibers.*—Few.
- *Ripens*—Even.
- *Flavor.*—Sub-acid; delicate.
- *Aroma.*—Wanting.
- *Eating quality.*—Good.
- *Color.*—Yellow (9–J–6, shading to 9–K–7), with red (3–L–11) at stone, becoming lighter (3–K–9) outwardly into flesh.

Stones:
- *Type.*—Cling; adheres to flesh over entire surface.
- *Size.*—Large to medium. Average length—1 3/16"; average breadth—1 1/16"; average thickness—11/16".
- *Form.*—Globose to oval.
- *Base.*—Oblique.
- *Hilum.*—Broad.
- *Apex.*—Rounded.
- *Sides.*—Equal.
- *Surface.*—Irregularly furrowed throughout; ridged toward apex; fitted throughout.
- *Ridges.*—Jagged; continuous.
- *Pits.*—Angular.
- *Ventral edge.*—Thick.
- *Dorsal edge.*—Full.
- *Color.*—Dark brown (8–L–6), with reddish (56–L–12) shading.

Use: Market; long distance shipping.

Keeping quality: Good.

Resistance to insects and diseases: Controlled by conventional spray practices for peaches and nectarines.
Shipping quality: Good.

The tree and its fruit herein described may vary in slight detail due to climatic and soil conditions under which the variety may be grown.

The following is claimed:

A new and distinct variety of nectarine tree, as illustrated and described, characterized by large size, yellow flesh, clingstone fruit whose exterior color is yellow almost entirely over-spread with red; said fruit being further characterized—as compared with the Red Grand nectarine—by ripening approximately two weeks later; and additionally characterized—as compared with the Le Grand nectarine—by ripening approximately one week later, but bearing fruit having a more attractive red exterior color.

No references cited.